United States Patent [19]
Yeo et al.

[11] Patent Number: 6,096,015
[45] Date of Patent: Aug. 1, 2000

[54] ABSORBENT ARTICLES HAVING IMPROVED SEPARATOR LAYER

[75] Inventors: Richard S. Yeo, Atlanta, Ga.; Benjamin M. Nolan, Elmer, N.J.; Kenneth Bononcini, Newfield, N.J.; Brian Boehmer, Cape May Court House, N.J.; Leonard Streeper, Richland, N.J.

[73] Assignee: Fibertech Group, Inc., Landisville, N.J.

[21] Appl. No.: 09/109,790

[22] Filed: Jul. 2, 1998

Related U.S. Application Data

[63] Continuation-in-part of application No. 08/759,405, Dec. 4, 1996, abandoned.

[51] Int. Cl.⁷ ..................................................... A61F 13/15
[52] U.S. Cl. ........................... 604/371; 604/378; 604/370
[58] Field of Search ..................................... 604/367, 370, 604/371, 378

[56] References Cited

U.S. PATENT DOCUMENTS 5,037,409  8/1991  Chen et al. .
5,522,810  6/1996  Allen, Jr. et al. .

FOREIGN PATENT DOCUMENTS 0 062 948 A1  10/1982  European Pat. Off. .
0 340 763 A1  11/1982  European Pat. Off. .
670 154 A2  8/1995  European Pat. Off. .
WO 95/17867  7/1995  WIPO .
WO 96/12460  5/1996  WIPO .
WO 96/33303  10/1996  WIPO .

*Primary Examiner*—John G. Weiss
*Assistant Examiner*—Dennis Ruhl
*Attorney, Agent, or Firm*—Pyle & Piontek

[57] ABSTRACT

An absorbent article such as a diaper has an outer layer of a porous fabric and an inner absorbent core. A separator layer of thermally bonded nonwoven fabric is positioned between the outer layer and the core to minimize rewet by liquids. The fibers of the nonwoven fabric of the separator layer have a diameter greater than 28 microns, and at least 5 crimps per extended inch, and the fabric has a porosity of about 90–95%, to provide superior rewet properties.

8 Claims, 4 Drawing Sheets

Figure 2

Sublayer Comparison Summary

Summary is based on average of 3 diaper testing.
Bulk, Bond pattern, fiber type & fiber finish included on summary

| Sample Code | total BW | denier / filament fiber #1 | fiber #2 | fiber diameter, u fiber #1 | fiber #2 | Diaper Wt. | Strike-through, sec. 1st | 2nd | 3rd | Rewet, grams 1st | 2nd | 3rd | Bulk mil | Bond Pattern | Fiber Finish | Fiber Type | Diaper test Performed | Multi Strike-Through, sec. 1st | 2nd | 3rd | AVG | | | crimp |
|---|---|---|---|---|---|---|---|---|---|---|---|---|---|---|---|---|---|---|---|---|---|---|---|---|
| Bauschlies | 50.0 | 9.9 | 6.0 | 39.3 | 30.6 | 42.3 | 13.8 | 12.3 | 14.6 | 0.1 | 0.2 | 1.2 | 34.0 | DH138 | Hy-repeat | Fibervision – PP | 3.0 | 2.8 | 2.5 | 3.6 | 2.96 | blend | | 13.0 |
| 143-177-9 | 62.0 | 9.0 | | 37.5 | | 42.9 | 10.6 | 10.6 | 11.7 | 0.1 | 0.1 | 2.2 | 37.0 | NGTS | 30530.0 | Fibervision – PP | 3.0 | 2.7 | 2.2 | 2.1 | 2.32 | 2 ply | | |
| 4147-0 | 40.0 | 3.0 | 10.0 | 21.7 | 32.0 | 42.8 | 7.90 | 8.50 | 10.5 | 0.2 | 0.6 | 4.4 | 53.0 | Thru-Air | | PP/PET | 3.0 | 2.2 | 2.0 | 2.70 | 2.31 | Fuzz | Layered | |
| 67CS0 | 35.0 | 8.0 | | 37.5 | | 41.5 | 16.0 | 14.0 | 15.9 | 0.1 | 0.3 | 4.7 | 17.0 | DH138 | Hy-Repeat | Fibervision – PP | 3.0 | 2.7 | 2.7 | 2.9 | 2.75 | | | 13.0 |
| 4138-0 | 40.0 | 3.0 | 10.0 | 21.7 | 32.0 | 42.1 | 8.80 | 8.60 | 9.50 | 0.4 | 0.5 | 5.50 | 44.0 | Thru-Air | | PP/PET | 3.0 | 1.7 | 1.5 | 1.8 | 1.68 | Fuzz | Blend | |
| 6829-0 | 43.0 | 6.0 | | 24.8 | | 42.5 | 9.9 | 10.8 | 13.1 | 0.1 | 1.0 | 5.9 | 35.0 | ABPET | | Dupont - PET | 3.0 | 2.30 | 2.4 | 2.30 | 2.32 | | | |
| 143-177-9 | 30.0 | 9.0 | | 37.5 | | 41.2 | 14.0 | 13.7 | 15.9 | 0.1 | 1.0 | 6.8 | 19.0 | NGTS | 30530.0 | Fibervision – PP | 3.0 | 3.1 | 3.20 | 4.0 | 3.40 | | | |
| 6853-0 | 15.0 | 3.0 | | 17.5 | | 44.4 | 18.9 | 20.0 | 25.6 | 0.1 | 0.70 | 7.9 | 10.0 | ABPET | | Dupont - PET | 3.0 | 3.3 | 3.9 | 4.4 | 3.85 | | | |
| 6714-8 | 15.0 | 4.4 | | 26.2 | | 41,610 | 20.3 | 25.5 | 43.0 | 0.1 | 0.5 | 8.1 | 8.0 | DVH400 | 15.0 | Denaldon - PP | 3.0 | 6.1 | 6.0 | 7.1 | 6.37 | | | |
| Fiberweb | 40.0 | 5.0 | 17.0 | 28.0 | 41.7 | 40.5 | 12.9 | 13.7 | 20.9 | 0.2 | 1.4 | 8.10 | 23.0 | Skew/Rec | | PP/PET | 3.0 | 3.0 | 2.7 | 3.2 | 2.97 | | Blend | |
| 156-177-9 | 20.0 | 3.0 | 9.0 | 21.7 | 37.5 | 42.6 | 19.7 | 20.9 | 26.1 | 0.1 | 0.5 | 8.3 | 10.0 | DH-138 | Hy-Repeat | Fibervision – PP | 3.0 | 3.4 | 4.8 | 5.5 | 4.57 | | Blend | |
| 6710.0 | 29.0 | 6.0 | 2.0 | 30.6 | 17.7 | 40.7 | 15.6 | 16.9 | 20.3 | 0.1 | 1.8 | 8.9 | 21.0 | NGTS | Perm Philic | Fibervision – PP | 3.0 | 4.0 | 3.5 | 3.84 | 3.79 | Blend | | 17.0 |
| meltblown 2 | 35.0 | 19.5 | | 65.2 | | 40.6 | 8.4 | 10.4 | 16.9 | 0.2 | 2.2 | 9.2 | 65.0 | | | Exxon 3446-PP | 3.0 | | | | | | | no crimp |
| 156-189-5 | 20.0 | 5.0 | 10.0 | 28.0 | 32.0 | 40.8 | 22.3 | 20.5 | 24.8 | 0.2 | 1.8 | 9.5 | 9.0 | DH138 | Hy-Repeat | Fibervision – PP | 3.0 | 3.5 | 3.7 | 3.8 | 3.66 | | | 21.0 |
| 4141.0 | 52.0 | 3.0 | | 21.7 | | 40.5 | 11.9 | 12.8 | 14.4 | 0.3 | 1.4 | 10.1 | 35.0 | Thru-Air | | PP/PET | 3.0 | 1.4 | 2.0 | 2.4 | 1.94 | Fuzz | | |
| Hugg/Cont. | 84.0 | 5.0 | | 27.6 | | 42.5 | 11.0 | 11.0 | 13.4 | 0.1 | 0.8 | 10.2 | 83.0 | Thru-Air | | Bico –PE/PET | 3.0 | 2.1 | 2.0 | 2.1 | 2.03 | | bico staple | |
| meltblown 1 | 35.0 | 4.0 | | 26.0 | | 41.7 | 13.0 | 16.0 | 31.9 | 0.1 | 3.7 | 10.6 | 31.0 | | | Exxon 3446-PP | 3.0 | 2.6 | 2.5 | 2.3 | 2.50 | | | |
| AmerNw | 19.0 | 3.0 | | 17.5 | | 43.8 | 15.8 | 17.6 | 20.4 | 0.2 | 0.6 | 12.1 | 14.0 | ABPET | | PET | 3.0 | 3.0 | 3.2 | 3.4 | 3.19 | | Layered | |
| Bauschwies | 40.0 | 2.0 | 6.0 | 17.7 | 30.6 | 42.2 | 16.1 | 17.2 | 18.5 | 0.2 | 4.3 | 13.3 | 28.0 | NGTS | Perm Philic | Fibervision – PP | 3.0 | | | | | | | 17.0 |

Fiber Diameters reported in micrometer (microns)
Fiber diameters calculated based on fiber specific gravity and denier where:

fiber diameter, u = square root ( denier / (specific gravity * 0.007707))

| | PP | PET | PE |
|---|---|---|---|
| Specific Gravity | 0.9 | 1.4 | 0.9 |

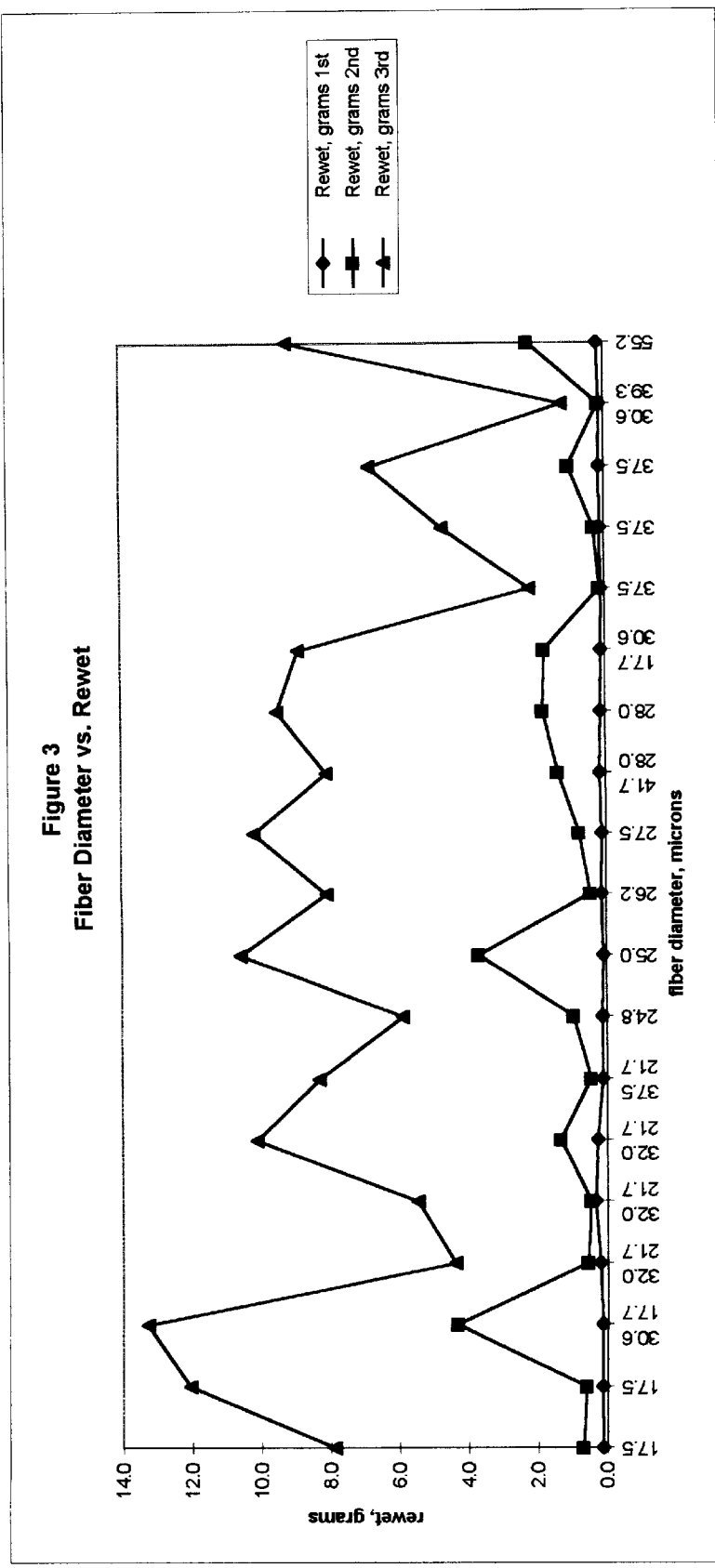

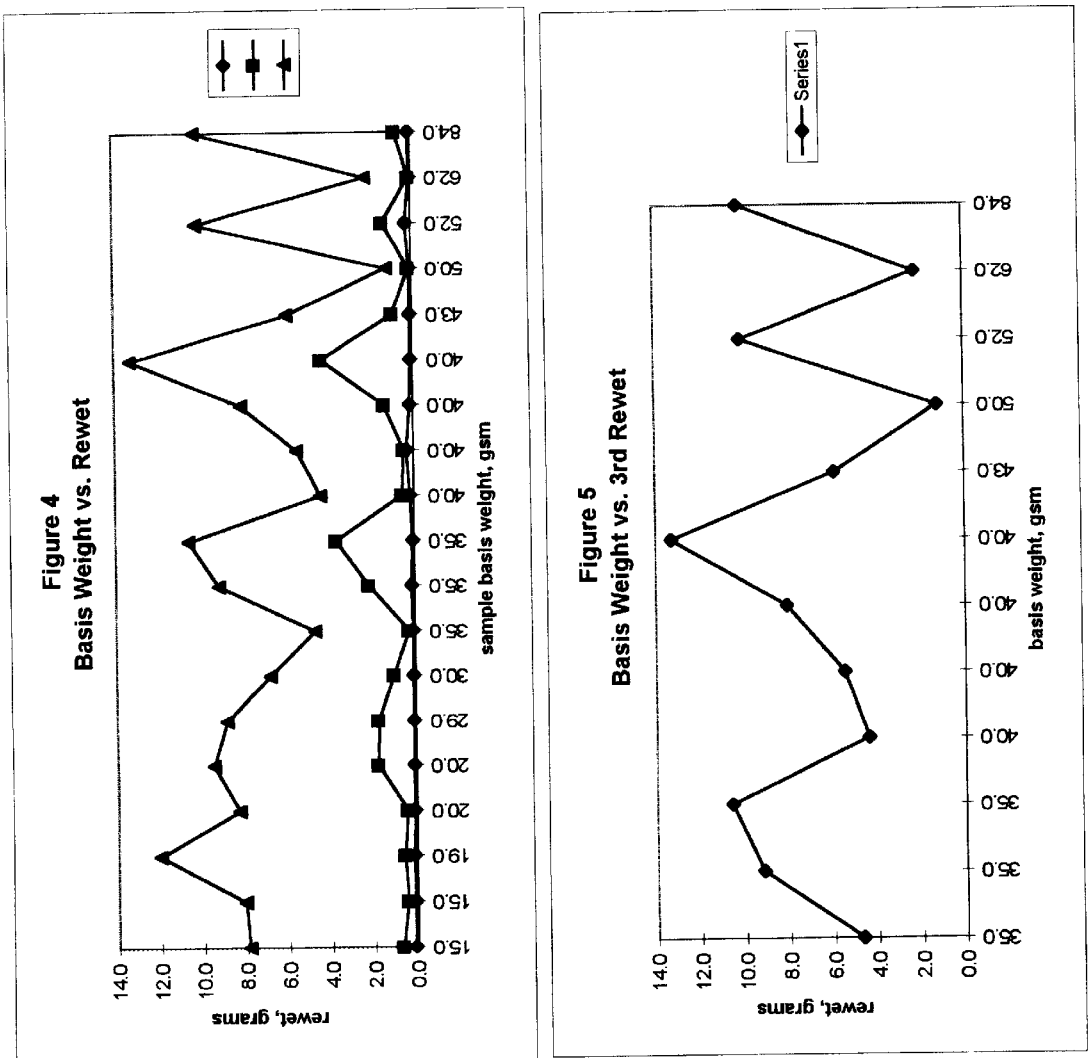

ABSORBENT ARTICLES HAVING IMPROVED SEPARATOR LAYER

This is a continuation-in-part patent application of U.S. patent application Ser. No. 08/759,405 filed on Dec. 4, 1996, now abandoned.

BACKGROUND OF THE INVENTION

This invention relates to absorbent articles and more particularly to layered disposable articles used, for example, as diapers, adult incontinence briefs and sanitary pads, in which a porous liquid absorbing layer of nonwoven fabric or porous film is disposed against the body of the user, and an inner layer is provided for absorption of liquids.

As originally designed, layered absorbent articles have included an inner or body facing cover of a porous fabric, an inner liquid absorbing layer or core, and an outer layer of liquid impervious film. In early products, the core was composed entirely of cellulose wadding or pulp, with the bulkiness or dry weight of the core being directly related to the maximum liquid absorption capacity.

More recently, proposals have been advanced to reduce the bulk of the core and to reduce the overall thickness of the absorbent product for several reasons, such as reduced shipping cost and storage space, and better conformability of the absorbent article or garment to the body of the user. A reduced absorbent core thickness has been accomplished primarily by increasing the density of the absorbent core and by adding up to about 40% by weight of a superabsorbing polymer, the latter being capable of absorbing many times of its weight of liquid. These changes, however, have inevitably led to a reduction in rate of absorption of liquid into the core, resulting in possible runoff and leakage of liquids.

In order to minimize the problems of runoff and leakage in low bulk absorbent articles, additional proposals have been made to employ a high bulk fabric as the upper layer, or to incorporate a transition layer of nonwoven fabric between the outer layer and the core. The purpose of this layer, also known as a sublayer or surge layer, is to hold or retain excess liquid for a time sufficient to allow the core to permanently absorb the liquid.

Various types of fabrics have been used as sublayers, including spunbonded fabrics and fabrics made of adhesively bonded fibers. Another type of fabric used for this purpose is low density lofty fabric having a high liquid void volume. These lofty fabrics, typically have a porosity of greater than 97 percent and are made from through-air thermally bonded bicomponent fibers to provide a sublayer having a high void volume.

In addition to liquid holding properties, another important criteria of a sublayer is to minimize a phenomena called rewetting. Rewetting occurs when liquid held in the sublayer or core migrates back through the porous cover or body side layer under normal contact pressures to wet or hydrate the surface of the skin. Because of their high porosity, lofty fabrics as described above tend to have poor rewet properties and also tend to add bulk to the product. It is well known that absorbent products which have a wet surface in contact with the skin can cause rashes and other skin irritations.

In view of the foregoing considerations, there is a continuing need to provide layered absorbent articles of the compact type which are not only capable of retaining liquid insults to be absorbed by the core, but also providing good separation and a significantly reduced amount of liquid or urine rewet to the top sheet.

SUMMARY OF THE INVENTION

In accordance with the present invention, an improved nonwoven fabric separator layer is provided for a liquid absorbent article. The absorbent article generally comprises a top porous sheet, an absorbent core, and the separator layer disposed between the top sheet and the core.

The separator layer comprises a majority of thermally bondable polymer staple fibers having a fiber diameter of at least 28 microns and preferably at least 35 microns. The fiber has at least 5 crimps per extended inch and preferably at least 10 crimps per extended inch.

The separator fabric is preferably formed by the steps of carding the fibers into a web on a moving conveyor and then point bonding the web by passage through hot calender rolls, one of which may be provided with a bonding pattern. The resulting fabric has a basis weight of from about 10 to about 55 grams per square meter (gsm), and the fibers or fabric are preferably treated with an agent, such as a surfactant, to render them hydrophilic or wettable by liquids, and to allow fast penetration of liquid into the core.

The relatively large degree of average diameter of fiber and the degree of crimp in the separator or sublayer fabric has an importance influence on the rapid transfer of liquids to the core while significantly reducing wetback to the cover layer and acting as a one-way valve. The separator fabrics of the present invention are particularly suitable for use in conjunction with high density cores and also allow for significant reduction in rewet irrespective of the density and absorption rate of the core.

BRIEF DESCRIPTION OF THE DRAWINGS

FIG. 2 is a table presenting test data demonstrating the benefits of the present invention;

FIG. 3 is a graph showing rewet performance against increasing fiber diameter;

FIG. 4 is a graph showing fabric basis weight against first, second and third insult rewet; and FIG. 5 is a graph showing fabric basis weight against third insult rewet.

DETAILED DESCRIPTION

Figure 1:
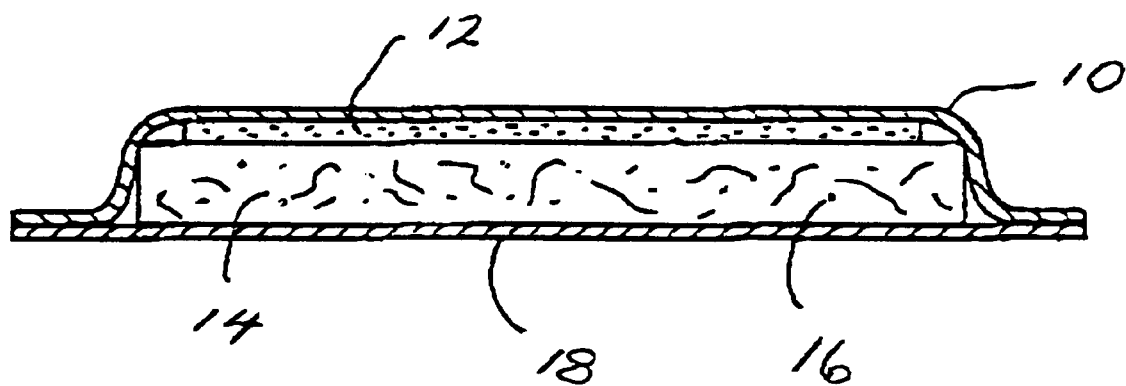
FIG. 1 is a sectional view through the layered absorbent article of the present invention showing the general arrangement of the various layers.

As shown in FIG. 1, the basic components of an absorbent product of the present invention comprise a porous top or body facing sheet of fabric or porous film 10, a liquid absorbing core 14, and a separator layer of nonwoven fabric 12 between the top sheet and the core.

The core 14 is conventional in nature and may comprise liquid absorbing cellulose fibers or pulp and/or a quantity of a superabsorbing polymer 16 (SAP) in powder, in particulate or fiber form. Various known core structures are available, which are capable of permanently absorbing liquids, even when the core is subjected to several doses of liquids. In addition, it is well known to provide the outer surface of the core with a liquid impervious layer 18, such as a layer of film, or a semipermeable layer of composite material to prevent outward transfer of liquids beyond the core.

The top sheet 10 is a conventional nonwoven fabric having good porosity and a soft surface. The top sheet 10 is preferably composed of heat bondable fibers, especially polyolefin fibers such as polypropylene, polyethylene, polybutylene, copolymers of any such polymers and mixtures and blends thereof It is also possible to fabricate the top sheet from thermally bondable bicomponent or multicomponent fibers, such as sheath-core or side-by-side fibers. In such case, the fiber will have a component with a lower melting point to allow thermal bonding.

Various known methods can be employed to form a web of the fibers and to bond a web of fibers into a fabric. A particularly suitable method comprises the steps of first carding the polyolefin fibers into a uniform random web, and then consolidating the web by passage between heated calender rolls, with one of the rolls having a raised bonding pattern. Other suitable methods of consolidation include hydraulic entanglement and through air bonding in which heated air is passed through the web, and spunbonding, in which continuous filaments are formed into a web and heat bonded. The cover layer 10 comprises fibers having a diameter of about seven to about twelve microns, and the fabric has a basis weight of about from 10 to about 40 gsm.

The separator fabric 12 preferably comprises at least 60% thermally bondable polymer fibers, preferably polypropylene fibers, with the fibers being treated with a surface active agent or surfactant to render it more hydrophilic. The fibers may be a blend of several different diameters, or fibers of different types and sizes may be provided in layers. Less than 40% of the fibers may comprise polyester, nylon, rayon, acrylic or bicomponent fibers.

The diameter and degree of crimp of the fibers of the separator fabric 12 relative to the topsheet 10 is very important in order to provide an acceptable rate of transfer of liquid toward and into the core 14, while at the same time, inhibiting flow back of liquids back through the topsheet. The fibers in the separator should have an average diameter of at least 28 microns and preferably at least 35 microns and should have an average diameter substantially greater than the fibers in the top layer. The fibers of the separator layer have a minimum of five crimps per extended inch and preferably at least ten crimps per extended inch. The basis weight of the fabric is from about 10 to about 55 gsm.

The nonwoven fabric of the separator layer 12 may be prepared by any suitable method, but the preferred method is by conventional carding and heat bonding techniques. The preferred method of bonding is by passing the unconsolidated web through a pair of heated calender rolls. Other possible consolidation methods include through air bonding and hydraulic entanglement, as well as spunbonding processes capable of imparting crimp to the filaments.

It will be noted that the layers 10, 12 and 14 have flat facing surfaces, and that these surfaces are brought into substantially full contact when assembled as layers in an absorbent article. The separator layer 12, while having a somewhat lower void volume, porosity, and liquid transfer rate than more lofty nonwovens, has a superior ability to prevent transfer of absorbed liquid back through the top sheet. The void volume of layer 12 is in the order of 10 to 25 cm$^3$/g, and the porosity is in the order of 90 to 95 percent.

TEST PROCEDURES

The following tests were employed to evaluate the liquid acquisition rate and rewet value of an absorbent article.

Unless otherwise specified, the same commercial diaper type (Ultrathin Huggies for Him Step 3, Kimberly-Clark, Dallas, Tex.) was employed. The core of these diapers contains a high ratio of superabsorbent polymer to pulp. The product has a top spunbonded nonwoven cover fabric having a basis weight of 22 gsm and a lofty sublayer of through-air bicomponent nonwoven fabric having a basis weight of 60 gsm.

The elastic members are removed from the diapers to allow the article to lie flat. With the exception of the control diapers, the topsheet and sublayer in these Huggies diapers were removed and the location of the sublayer was marked. The test separator materials were cut to the same dimension as the Huggies sublayer and were placed on top of the absorbent core at the same location of the Huggies sublayer. A thermal bonded polypropylene carded web (18 gsm) sold under the trade brand of 6788 by PGI Nonwovens was placed on top of the test separator layer. A pressure loading of 0.5 psi is applied to the middle of the test sublayer sample. An opening area of 0.8 square inch is provided and located at the center of the pressure load to allow a simulated urine solution to be introduced into the diaper core through the topsheet and test separator samples. The simulated urine was product JA-00131-000-01 supplied by Endovations Inc. of Reading, Pa. A funnel is positioned on top of the opening area of the pressure load and a total of 100 ml of simulated urine was introduced into the diaper core. The time for the liquid to completely enter the absorbent structure is then measured and is termed the "first insult strike-through" of the sample.

The 0.5 psi pressure load is continued applied on the diaper for 5 minutes. The pressure is momentarily removed, a preweighed sample of absorbent filter paper (Eaton-Dikeman Filter Paper #631) approximately 5"×5" is inserted on top of the topsheet around the test area, and the 0.5 psi pressure loading is reapplied to the sample for a period of 2 minutes. The filter paper is removed and reweighed, and the amount of liquid absorbed by the fiber paper is termed the "first insult rewet" of the sample.

The above procedure was repeated two more times to obtain the second and third insult strikethrough and rewet of the sample.

The following examples 1–7 are designed to illustrate particular embodiments of the present invention and to teach one of ordinary skill in the art the manner of carrying out the present invention.

EXAMPLES 1–3

In Example 1, the Huggies sample is tested in its original condition without alteration. In Example 2, the Huggies topsheet was removed and replaced with the above 6788 fabric. The original thru-air bond carded web sublayer remained in the diaper during testing. In Example 3, both the original topsheet and sublayer were removed. A layer of brand 6788 is placed on top of the absorbent core. In this situation, the diaper is tested without a sublayer. The tests results are listed in Table 1.

EXAMPLE 4

A 40 gsm basis weight bonded carded web comprising 31 micron, crimped staple fibers under the trade brand of Hi Comfort Philip available from Danaklon Americas of Athens, Ga., was made using a carding machine. The fibers had an average length of 1.5 inches. The fibers had a natural helical crimp ranging from about 7 to about 11 crimps per extended inch counting 1 crimp per repeat cycle of the helical fibers in accordance with ASTM D-3937. The line speed of the carding machine was 400 feet per minute. The carded web was fed through a pair of heat calender rolls. The pattern has a bond area of about 24% and a pin density of 400 pins per square inches. The fabric had a porosity of 90.3%. The fabric was then tested as the separator layer with the Huggies core.

EXAMPLE 5

A 40 gsm basis weight bonded carded web comprising 37 micron, crimped staple fibers under the trade brand of Hi Comfort Philic available from Danaklon Americas, Inc. of Athens, Ga., was made using a carding machine. The fibers had an average length of 1.5 inches. The fibers had a natural helical crimp ranging from about 7 to about 11 crimps per extended inch, counting 1 crimp per repeat cycle of the helical fibers in accordance with ASTM D-3937. The line speed of the carding machine was 400 feet per minute. The carded web was fed through a pair of heated calender rolls. The pattern had a bond area of about 24% and a pin density of 400 pins per square inches. The fabric has a porosity of 91.5%. The fabric was then tested as separator layer with the Huggies core.

EXAMPLE 6

A 40 gsm basis weight bonded carded web comprising 43 micron, crimped staple fibers under trademark Hi Comfort Philic available from Danaklon Americas of Athens, Ga., was made using a carding machine. The fibers had an average length of 1.5 inches. The fibers have a natural helical crimp ranging from about 7 to about 11 crimps per extended inch, counting 1 crimp repeat cycle of the helical fibers in accordance with ASTM D-3937. The line speed of the carding machine was about 94 feet per minute. The carded web was fed through a pair of heat calender rolls. The pattern has a bond area of about 24% and pin density of 400 pins per square inch. The fabric had a porosity of 93.3%. The fabric was then tested as a sublayer material. The results of the tests of the fabrics of Examples 4–6 are also shown in Table I.

TABLE I

| Example No. | Strike-Through (Sec) | | | Rewet (gm) | | | |
|---|---|---|---|---|---|---|---|
| | 1st insult | 2nd | 3rd | 1st insult | 2nd | 3rd | Total |
| 1 | 69.5 | 79.5 | 87.3 | 0.10 | 0.12 | 3.34 | 3.56 |
| 2 | 73.6 | 78.9 | 88.6 | 0.14 | 2.06 | 5.53 | 7.73 |
| 3 | 213.5 | 199.8 | 217.4 | 0.19 | 2.61 | 7.7 | 10.56 |
| 4 | 111.1 | 134.8 | 155.8 | 0.16 | 0.23 | 1.56 | 1.95 |
| 5 | 84.8 | 113.1 | 131.3 | 0.21 | 0.22 | 0.33 | 0.76 |
| 6 | 122.1 | 140.1 | 164.5 | 0.15 | 0.21 | 0.39 | 0.75 |

From a review of Examples 1–6, which use the same commercial core, the separator fabric resent invention allows a significant reduction in rewet, with an average of less than two of rewet liquid, and usually less than one gram, after three 100 ml liquid insults in on.

EXAMPLE 7

An expanded study including a broader range of fiber sizes and compositions confirms that fibers exceeding five (5) denier (or having a diameter of 28 microns or more) for a consolidated carded staple fiber fabric obtains the claimed performance improvement in rewet.

The results of the tests of the fabrics of Example 7 are summarized in Table II below according to increasing fiber denier per filament (dpf) and fiber diameter (in microns) relative strike-through time (in seconds) and third rewet (in grams). The testing is more fully set forth in FIG. 2 and is based on an average of three (3) diaper testing.

For purposes of analyzing Example 7, the commercial competitive sample from the leading brand Huggies was again used as a competitive benchmark. The test method used substantially the same as described above, except that a pressure loading of 0.5 psi was not applied to the middle of the test sublayer sample. Rather, a simulated urine solution, here saline solution, was poured onto the diaper core through a tube onto the topsheet and test separator sheet samples. A total of 80 ml of simulated urine was introduced into the diaper core. The time for the liquid to completely enter the absorbent structure was measured as the "first insult strike-through" of the sample. As shown, the Huggies brand resulted in a third insult rewet of 10.2 grams. Therefore, any result below 8 grams of rewet on the third insult, representing a nominal 20% improvement in performance on a leading commercial product, was considered a significant improvement.

TABLE II

| Sample Code | denier | | | fiber diameter, u | | Bulk, Bond pattern, fiber type & fiber finish included on summary | | | | | | |
|---|---|---|---|---|---|---|---|---|---|---|---|---|
| | total BW | per filament | | | | Diaper Wt. | Strike through, sec. | | | Rewet, grams | | |
| | | fiber #1 | fiber #2 | fiber #1 | fiber #2 | | 1st | 2nd | 3rd | 1st | 2nd | 3rd |
| 6853-0 | 15.0 | 3.0 | | 17.5 | | 44.4 | 18.9 | 20.0 | 25.6 | 0.1 | 0.70 | 7.9 |
| Amer/NW | 19.0 | 3.0 | | 17.5 | | 43.8 | 15.8 | 17.6 | 20.4 | 0.2 | 0.6 | 12.1 |
| 6714–8 | 15.0 | 4.4 | | 26.2 | | 41.610 | 20.3 | 25.5 | 43.0 | 0.1 | 0.5 | 8.1 |
| 156–189-6 | 20.0 | 5.0 | | 28.0 | | 40.8 | 22.3 | 20.5 | 24.8 | 0.2 | 1.8 | 9.5 |
| meltblown | 35.0 | 5.0 | | 28.0 | | 41.7 | 13.0 | 16.0 | 31.9 | 0.1 | 3.73 | 10.6 |
| Hugg/Cont. | 84.0 | 5.0 | | 27.5 | | 42.5 | 11.0 | 11.0 | 13.4 | 0.1 | 0.8 | 10.2 |
| 6829-0 | 43.0 | 6.0 | | 24.8 | | 42.5 | 9.9 | 10.8 | 13.1 | 0.1 | 1.0 | 5.9 |
| 143–177–9 | 30.0 | 9.0 | | 37.5 | | 41.2 | 14.0 | 13.7 | 15.9 | 0.1 | 1.0 | 6.8 |
| 67CSO | 35.0 | 9.0 | | 37.5 | | 41.5 | 15.0 | 14.0 | 15.9 | 0.1 | 0.3 | 4.7 |
| 143–177–9 | 62.0 | 9.0 | | 37.5 | | 42.9 | 10.6 | 10.6 | 11.7 | 0.1 | 0.1 | 2.2 |
| 156–195–10 | 50.0 | 9.9 | 6.0 | 39.3 | 30.6 | 42.3 | 13.8 | 12.3 | 14.6 | 0.1 | 0.2 | 1.2 |
| Bauschvlies | 40.0 | 2.0 | 6.0 | 17.7 | 30.6 | 42.2 | 16.1 | 17.2 | 18.5 | 0.2 | 4.3 | 13.3 |
| 156–177–9 | 20.0 | 3.0 | 9.0 | 21.7 | 37.5 | 42.6 | 19.7 | 20.9 | 25.1 | 0.1 | 0.5 | 8.3 |
| Fiberweb | 40.0 | 5.0 | 17.0 | 28.0 | 41.7 | 40.6 | 12.9 | 13.7 | 20.9 | 0.2 | 1.4 | 8.10 |
| 6710.0 | 29.0 | 6.0 | 2.0 | 30.6 | 17.7 | 40.7 | 15.6 | 16.9 | 20.3 | 0.1 | 1.8 | 8.9 |
| 4138.0 | 40.0 | 3.0 | 10.0 | 21.7 | 32.0 | 42.1 | 8.80 | 8.60 | 9.50 | 0.4 | 0.5 | 5.50 |
| 4147.0 | 40.0 | 3.0 | 10.0 | 21.7 | 32.0 | 42.8 | 7.90 | 8.50 | 10.5 | 0.2 | 0.6 | 4.4 |
| 4141.0 | 52.0 | 3.0 | 10.0 | 21.7 | 32.0 | 40.5 | 11.9 | 12.8 | 14.4 | 0.3 | 1.4 | 10.1 |

As contemplated by the present invention, a blend of fibers used to create the sublayer should have one of the fibers of at least 5 denier and crimp. Additionally, if the sublayer or separator layer is made of two individual layers, one of the individual layers should have fiber deniers greater than 5. The data set forth in FIG. 2 and Table II indicates that the benefits of the present invention are independent of the method of web consolidation, that is, either pattern bonded or through air. Crimp is also important to fabric performance. While samples with high crimp and low denier failed to achieve superior performance, it was observed that a high denier, low crimp fabric did not obtain the desired exceptional performance, supporting the need for crimping. For example, Meltblown Sample Nos. 1 and 2, were at 25 and 5.2 microns, well above the fiber size expected to offer the desired exceptional performance. However, these sample have no crimp and did not obtain the desired exceptional performance (only 10.6 and 9.2 gram at third insult rewet, respectively).

Referring to FIG. 3, the results are plotted according to increasing fiber diameter, in microns. It can be observed that all samples perform similarly after the first and second rewets. Substantial difference in performance occurs after the third insult. Again using 8 grams of rewet as the desired exceptional performance, all samples falling below that value fit the predictive model of the present invention. Although a single sample, No. 6710, fits the model of higher fiber thickness and crimp without providing the significant improvement in performance, the model is still supported by 18 other examples obtained from industry as well as internal samples.

To confirm that basis weight differences were not overwhelming the sensitivity of the model, third insult rewet is presented against sublayer basis weight in FIGS. 4 and 5. Again, using 8 grams of rewet as exceptional performance, one notes first that the best performance is for fabrics greater than 20 gsm. However, there are several examples at the 35 gsm and 40 gsm level where the superior performance at a given basis weight is demonstrated only by fabrics that fit the limitations of the present invention. Finally, one of the worst performers is the Huggies sample, which coincidentally has the highest sublayer basis weight of all samples tested.

What is claimed is:

1. An absorbent layered article comprising a porous topsheet, an absorbent core, and a separator layer disposed in contact between said top sheet and said core, said separator layer comprising a nonwoven fabric of at least 60% polymer fibers bonded by heat calendering, said fibers having a hydrophilic surface, an average fiber diameter of at least 28 microns and at least five crimps per extended inch.

2. The absorbent layered article of claim 1 wherein said fibers have an average fiber diameter of at least 35 microns.

3. The absorbent layered article of claim 1 wherein said fibers have at least ten crimps per extended inch.

4. The absorbent layered article of claim 1 wherein said separator layer comprises said nonwoven fabric having fibers of more than one diameter.

5. The absorbent layered article of claim 1 wherein less than 40% of said fibers are selected from the group consisting of polyester, nylon, rayon, acrylic and bicomponent fibers.

6. The absorbent layered article of claim 1 wherein said polymer fibers are polypropylene fibers.

7. The absorbent layered article of claim 1 wherein said separator layer has a porosity of from about 90 to about 95 percent.

8. The absorbent layered article of claim 1 wherein said top sheet is a nonwoven fabric comprising fibers having an average diameter less than the average diameter of the fibers of the separator layer.

* * * * *